United States Patent [19]

Stambrook et al.

[11] Patent Number: 4,792,520
[45] Date of Patent: Dec. 20, 1988

[54] METHODS AND KITS FOR IDENTIFYING MUTAGENIC AGENTS AND MOLECULAR MUTATIONS IN DNA IN MAMMALIAN CELLS

[75] Inventors: Peter J. Stambrook, Cincinnati, Ohio; Jay A. Tischfield, Augusta, Ga.

[73] Assignees: University of Cincinnati, Cincinnati, Ohio; Medical College of Georgia Research Institute, Augusta, Ga.

[21] Appl. No.: 580,876

[22] Filed: Feb. 16, 1984

[51] Int. Cl.[4] .......................... C12Q 1/68; C12Q 1/02; C12Q 1/04
[52] U.S. Cl. ............................................. 435/6; 435/4; 435/29; 435/34; 935/55; 935/70; 935/71; 935/84
[58] Field of Search .................. 435/4, 5, 6, 29, 34; 935/55, 70, 71, 84

[56] References Cited

U.S. PATENT DOCUMENTS

| | | | |
|---|---|---|---|
| 4,072,574 | 2/1978 | Loeb et al. | 435/6 |
| 4,302,535 | 11/1981 | Skopek et al. | 435/29 |
| 4,345,026 | 8/1982 | Lew | 435/6 |
| 4,359,535 | 11/1982 | Pieczenik | 435/5 |
| 4,469,786 | 9/1984 | Garro et al. | 435/5 |
| 4,532,220 | 7/1985 | Lavi | 435/6 |

FOREIGN PATENT DOCUMENTS 0062237 10/1982 European Pat. Off. ............... 435/6

OTHER PUBLICATIONS

Sims et al., Apr. 7, 1972, Science, vol. 176, pp. 47–49.
Clive et al; Mutation Research, (1979), vol. 59, pp. 61–108.
Stambrook, P. J. et al, *Somatic Cell and Molecular Genetics*, 10(4):359–367, (1984).
Dush, M. K. et al, *Advances in Gene Technology: Human Genetic Disorder*, ICSU Short Reports, 1:160–161, (1984).
Srivatsan, E. S. et al, *Cytogenet, Cell Genet*, 38:227–234, (1984).

(List continued on next page.)

Primary Examiner—Robert J. Warden
Assistant Examiner—Jack Spiegel
Attorney, Agent, or Firm—Wood, Herron & Evans

[57] ABSTRACT

A new and improved cell assay has been developed for mutagens and potential carcinogens to precisely identify the predominant type of mutation(s) each such compound induces in the DNA of cells. The test utilizes, for example, a selectable genetic marker such as adenine phosphoribosyltransferase (APRT) which is now extensively characterized on the DNA, protein and cellular phenotype levels. Specific mutations such as transitions, transversions, point insertions or point deletions are engineered at specific known sites in a mouse APRT gene deduced from the determined gene sequence, such that the gene cannot be properly expressed. These mutant genes are then introduced into non-reverting APRT deficient mammalian cells. These hybrid constructs represent the basic test medium for detection of mutagenic activity. The tester cells are treated with mutagens known to preferentially induce specific DNA mutations in mammalian cells. Reversion within the appropriate tester cell culture detected by growth in selection medium or other detection systems, will confirm or refute the mode of action of these mutagens. As an additional approach for the identification of mutagens that produce frameshifts, the amino acid sequences of major frameshift peptides have been determined from the nucleotide sequence of the mouse APRT gene. These frameshift peptides are synthesized and individually used to elicit antisera. Mutant colonies, arising as a consequence of frameshift mutation, are identified in situ by virtue of their binding one of the specific antisera which are coupled to a color-development assay. Additionally, methods for identifying mutagens which produce mutations at the APRT locus, and which exert their effect by inducing DNA rearrangements, transpositions or excision are employed. The tester lines and reagents enable the exact nature of mutation that any mutagen produces in cells to be rapidly established. Further, portions of the nucleotide sequence of a mouse APRT DNA strand as well as its encoded amino acid sequence are disclosed.

71 Claims, 3 Drawing Sheets

OTHER PUBLICATIONS

Tischfield, J. A. & Rubble, F. H., *Proc. Natl. Acad. Sci. U.S.A.*, 71(1):45–49, (Jan. 1974).
Gillam, S. et al, Gene, 12:129–137, (1980).
Southern, E. M., J. Mol. Biol., 98:503–517, (1975).
Rigby, P. W. J. et al, J. Mol. Biol., 113:237–251, (1977).
Denhardt, D. T., *Biochemical and Biophysical Research Communications*, 23(5):641–646, (1966).
Ishiura, M. et al, Molecular and Cellular Biology, 2(6):607–616, (Jun. 1982).
Stambrook, P. J., J. Mol. Biol., 82:303–313, (1974).
Tischfield, J. A. et al., Analytical Biochemistry, 53:545–554, (1973).
Sutcliffe, J. G. et al, Science, 219:660–665, (Feb. 1983).
Green, N. et al, Cell, 28:477–487, (Mar. 1982).
Tischfield, J. A. et al, *Molecular and Cellular Biology*, 2(3):250–257, (Mar. 1982).
Maniatis, T. et al, Cell, 15:687–701, (Oct. 1978).
Benton, W. D. & David, R. W., Science, 196:180–182, (Apr. 1977).
Sikela, J. M. et al, Gene, 22:219–228, (1983).
Chemicals and Genetic Damage, Nature, vol. 301:653, (Feb. 1983).
Southern, P. J. & Berg, P., *Journal of Molecular and Applied Genetics*, 1(4):327–341, (1982).
Huberman, E. & Sachs, L., *Int. J. Cancer*, 13:326–333, (1974).
Wallace, R. B. et al, *Nucleic Acids Research*, (9)15:3647–3656, (1981).
Zarucki-Schulz, T. et al, *The Journal of Biological Chemistry*, 257(18):11070–11077, (Sep. 1982).
Wigler, M. et al, Proc. Natl. Acad. Sci., 76(3): 1373–1376, (3/79).
Summary and Conclusions, In: Identifying and Estimating the Genetic Impact of Chemical Mutagens, (Ed. N. Grossblatt).
National Academy Press, Washington, D.C., pp. 1–253 (1983).
Academy Press, 2101 Constitution Ave., N.W., Washington, D.C. 20418.
Maniatis, T. et al: Isolation of Bacteriophage λ and Plasmid DNA, In: *Molecular Cloning, A Laboratory Manual*, Cold Spring Harbor Laboratory, pp. 1–521, (1982).

The cross-hatched box indicates the position of the gene. The numbers indicate distances in kilobases.
H = HindIII; Pvu = PvuII; B = BamH1; E - EcoR1; Sph = SphI.

Mouse APRT cDNA and Amino Acid Sequence

```
                    20                                40                                 60
         ile ser pro leu leu lys asp pro asp ser phe arg ala ser ile arg leu leu ala ser
(POLY G)AT ATC TCG CCC CTC TTG AAA GAC CCG GAC TCC TTC CGA GCT TCC ATC CGC CTC TTG GCC AGT
                        80                               100                                120
         his leu lys ser thr his ser gly lys ile asp tyr ile ala gly leu asp ser arg gly phe leu
         CAC CTG AAG TCC ACG CAC AGC GGC AAG ATC GAC TAC ATC GCA GGT CTA GAC TCC AGG GGC TTC CTG
              140                              160                                180
         phe gly pro ser leu ala gln glu leu gly val gly cys val leu ile arg lys gln gly lys leu
         TTT GGC CCT TCC CTA GCT CAG GAG CTG GGC GTG GGC TGT GTG CTC ATC CGG AAA CAG GGG AAG CTG
              200                              220                                240                  260
         pro gly pro thr val ser ala ser tyr ser leu glu tyr gly lys ala glu leu glu ile gln lys
         CCG GGC CCC ACT GTG TCA GCC TCC TAT TCT CTG GAG TAT GGG AAG GCT GAG CTG GAA ATC CAG AAA
                             280                              300                                320
         asp ala leu glu pro gly gln arg val val ile val asp asp leu leu ala thr gly gly thr met
         GAT GCC TTG GAA CCC GGG CAG AGA GTG GTC ATT GTG GAT GAC CTC CTG GCC ACA GGA GGA ACC ATG
                        340                              360                                380
         phe ala ala cys asp leu leu his gln leu arg ala glu val val glu cys val ser leu val glu
         TTT GCG GCC TGT GAC CTG CTG CAC CAG CTC CGG GCT GAA GTG GTG GAG TGT GTG AGC CTG GTG GAG
                        400                              420                                440
         leu thr ser leu lys gly arg glu arg ser gly pro ile pro phe phe ser leu leu gln tyr asp
         CTG ACC TCG CTG AAG GGC AGG GAG AGG CTA GGA CCT ATA CCA TTC TTC TCT CTC CTC CAG TAT GAC
         460
         ter                  480             500                  520
         TGA GGAGCTGGCTAGATGGTCACACCCCTGCTCCCAGCAGCACTAGGAACTGCTTGGTGGCTCAGCCTAGGCGCCTAAGT 540                  560              580                     600
         GACCTTTGTGAGCTACCGGCCGCCCTTTTGTGAGTGTTATCACTCATTCCTTTGGTCAGCTGATCCGCCGTGCCTGT 620                  640              660                     680
         GGACCCCTGGATCCTTGTACTTTGTACACGTGCCACACACCCTGGAGCATAGCAGAGCTGTGCTACTGGAGATCAAT

700
         AAACCGTTTTGATATGCAAAAAA(POLY C)
```

FIG. 2

METHODS AND KITS FOR IDENTIFYING MUTAGENIC AGENTS AND MOLECULAR MUTATIONS IN DNA IN MAMMALIAN CELLS

BACKGROUND OF THE INVENTION

Many environmental chemicals are mutagens and potential carcinogens that may inflict heritable genetic damage. There already exist some 70,000 synthetic chemicals in commercial use, with another 1,000 new ones synthesized each year. Thus, the need for effective mutagen screening is clear. A recent National Academy of Sciences (NAS) report, commissioned by the Environmental Protection Agency, underscores this need and the limitations of currently available mutagenicity assays. See Summary and Conclusions, In: *Identifying and Estimating the Genetic Impact of Chemical Mutagens*, (Ed N. Grossblatt.), National Academy Press, Washington, D.C. pp. 1-138, (1983). The Salmonella/Microsome test developed by Ames and his co-workers is the most widely used assay to identify such compounds, and it detects about 90% of carcinogens examined. Possible reasons for obtaining false negatives and false positives have been considered in the literature. To complement the bacterial tests, several mutagenicity assays utilizing cultured mammalian cells have been developed. These have been useful in identifying several mutagens that the bacterial test fails to detect and they provide a basis for comparing the potential mutagenicity of different agents in eukaryotic cells.

One shortcoming of the mammalian cell assays in use is that, unlike the Ames test, none can determine the type of mutation a mutagen produces. Most of what is known about the types of mutations induced by mutagens is derived from bacterial test systems, and what little understanding we have of the effects of mutagens on the DNA of mammalian cells is often based on extrapolation. Confirmation of such information is frequently circuitous and difficult to obtain. Unfortunately, an argument that a mutagen acts in mammalian cells by inducing frameshifts or transitions is most often by extrapolation from its effects on bacterial cells. The need for more rigorous assessment of the kinds of damage that environmental mutagens can inflict upon mammalian DNA is emphasized by the NAS report. As noted in an editorial in Chemicals and Genetic Damage, *Nature*, 301:653 (1983), the ideal would be that there should be such a full understanding of what happens metabolically to particular chemicals in mammalian cells such as germ and somatic cells, and such a full catalog of possible interactions with nuclear DNA, that the prediction of mutagenicity would be possible.

SUMMARY OF THE INVENTION

In brief, the present invention seeks to alleviate the above-indicated problems and shortcomings of the present state of the art and is directed to new and improved methods for rapidly determining substance or radiation mutagenicity, and more particularly, mutagenicity to mammalian cell. The methods will not only identify agents which are mutagenic, but will also reveal whether the mutations induced are due to a base substitution, a frameshift, DNA transposition, loss or excision, or DNA rearrangement. To accomplish the above, a mouse APRT gene or other selectable gene which has been cloned will be utilized. A kit of tester cells is provided by the invention for identifying a mutagenic agent in mammalian cells and the molecular nature of mutation caused thereby.

In one embodiment of the present invention, a method of identifying a mutagenic agent which causes base substitution mutation in cells is provided. The method comprises using in vitro site specific mutagenesis to construct a cloned recessive gene having a base substitution at a specific site rendering said gene or its product non-functional, introducing said mutated gene into recessive phenotype non-reverting cells to produce transfected cells, subjecting said transfected cells to the mutagenic agent for a sufficient amount of time to induce mutagenesis at said specific site, and adding cell culture medium which selects for dominant cells which have undergone reversion at said site for identifying the base substitution mutation caused by the mutagenic agent.

In another embodiment of the present invention, a method of identifying a mutagenic agent which causes frameshift mutation(s) in cells is provided. The method comprises subjecting wild-type dominant phenotype cells to the mutagenic agent for a sufficient amount of time to induce frameshift mutagenesis causing said mutagen treated cells to generate frameshift peptides, adding cell culture medium which selects for heterozygous or recessive phenotype cells, and exposing said selected cells to an antibody directed against said frameshift peptides generated from said frameshift mutagenesis for identifying said frameshift mutagenesis caused by said mutagenic agent.

In still a further embodiment of the present invention, another method of identifying a mutagenic agent which causes frameshift mutation in cells is achieved. The method comprises using in vitro site specific mutagenesis to construct a cloned recessive gene having a frameshift mutation by insertion or deletion of a nucleotide at a specific site, introducing said mutated gene into recessive phenotype non-reverting cells to produce transfected cells, subjecting said transfected cells to the mutagenic agent for a sufficient amount of time to induce frameshift mutation, and adding cell culture medium which selects for dominant phenotype cells for identifying phenotypic reversion as a consequence of a frameshift mutation caused by the mutagenic agent.

In another embodiment of the present invention, a method of identifying a mutagenic agent which induces or facilitates DNA transposition is provided. The method comprises providing a cell line hemizygous or heterozygous at a target locus, rendering said hemizygous or heterozygous cell recessive at said locus by insertion of a retrovirus proviral DNA or other transposable DNA at or near said target locus, subjecting said recessive cells to the mutagenic agent for a sufficient amount of time to induce reversion by transposition, excision or loss of proviral or other transposable DNA, and adding cell culture medium which selects for dominant phenotype cells for identifying the DNA transposition, loss or excision induced by the mutagenic agent.

In another embodiment of the present invention, a method of identifying a mutagenic agent which causes DNA rearrangements in cells is provided. The method comprises subjecting wild-type dominant phenotype cells to the mutagenic agent for a sufficient amount of time to induce DNA rearrangements, adding cell culture medium that selects for heterozygous or recessive phenotype cells, isolating DNA from said recessive cells, digesting said DNA with each of several restriction enzymes known to produce characteristic sets of restriction patterns in DNA from wild-type cells by DNA blot analysis using labeled cloned DNA as a probe, and comparing restriction patterns of DNAs from said heterozygous or recessive cells with those of wild-type DNAs.

The invention also provides a mouse APRT DNA strand comprising a nucleotide sequence of adenine (A), guanine (G), thymine (T), and cytosine (C) nucleotides having the sequence as shown in FIG. 2 hereinafter. Further, an amino acid sequence as shown in FIG. 2 that is encoded for by the DNA strand of FIG. 2 is disclosed.

It is to be understood that a fundamental difference between the tests described herein and previously described tests using prokaryotic or eukaryotic cells is that previous tests utilize wild-type or genetically selected cells wherein the invention herein described critically depends upon genetically constructed cells. Additionally, the mutagenic agents that can be identified by using the methods disclosed herein can include, for example, compounds, substances, ultraviolet light, ionizing radiation or high energy radiation. Still further, the methods disclosed herein preferentially employ the cloned mouse APRT gene for constructing a series of tester cell lines that will identify mutagens and define the type(s) of mutation they produce. Thus, the invention provides a test method system and a kit of tester cells for detecting a mutagenic agent and the molecular nature of the mutation caused thereby.

The above and other features and advantages of the invention, including various novel details of construction and materials used, will now be more particularly described with reference to the drawings.

BRIEF DESCRIPTION OF THE DRAWINGS

Reference is made to the accompanying drawings in which there are shown illustrative embodiments of the invention from which its novel features and advantages will be apparent.

FIG. 2 is illustrative of an embodiment of the invention of the partial mouse APRT cDNA nucleotide sequence and the amino acid sequence that it encodes.

It will be understood that the particular drawings embodying the invention are shown by way of illustration only and not as a limitation of the invention. The principles and features of this invention may be employed in various and numerous embodiments without departing from the scope of the invention.

DETAILED DESCRIPTION OF THE INVENTION

Figure 3:
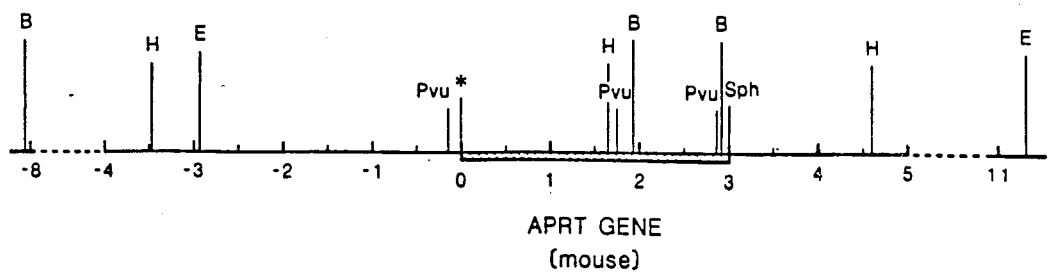
FIG. 3 is illustrative of an embodiment of the invention of regions flanking the mouse APRT gene for digestion by restriction enzymes.

The test system of this invention, as exemplified herein, involves the establishment of a series of tester cell lines using the adenine phosphoribosyltransferase (APRT) locus as one target of choice for analyzing mutagenic effects. The mouse APRT gene is particularly suited for use in this invention since it is small, i.e., less than 3 Kb, and, therefore, easy to manipulate and transfect. As a dominant selectable marker upon reversion, it provides sensitive backward cell selection to complement the forward adenine analog-mediated selection. As part of the test system, the mouse APRT gene has been cloned and characterized which is illustrated in FIGS. 1-3.

Figure 1:
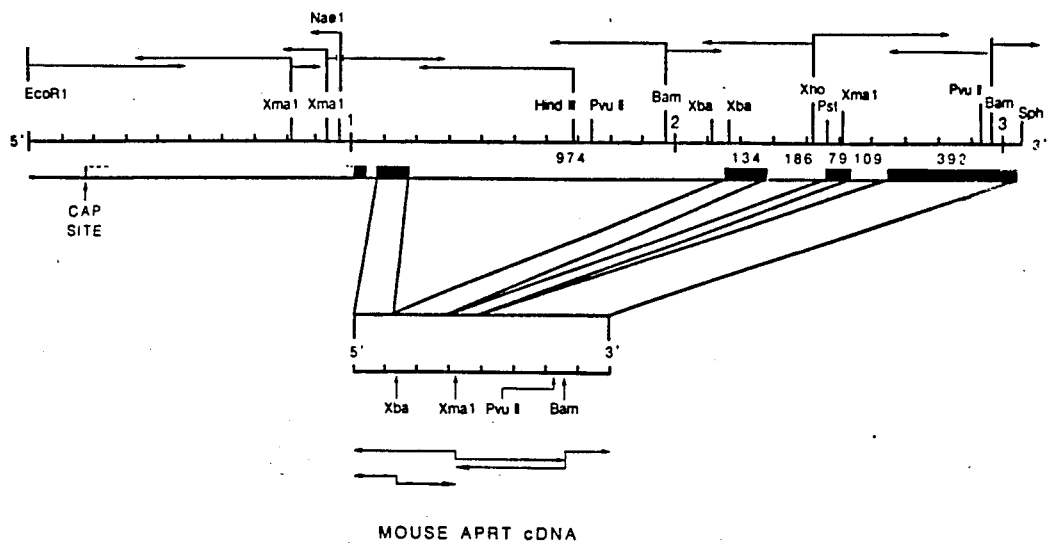
FIG. 1 is illustrative of an embodiment of the invention of the internal restriction endonuclease digestion pattern of the wild-type mouse APRT gene.

Referring now to FIG. 1, the 3' end of the cDNA was determined after identification of a short poly A tail and the polyadenylation signal AATAAA 20 bp upstream. The genomic DNA comprising the 3.1 kb fragment has coding regions that are colinear with the cDNA (indicated as blackened boxes in the figure), and as expected, it also contains the polyadenylation signal. The genomic fragment of pSAM-1 (shown in FIG. 1) extends only three nucleotides beyond the 3' end of cDNA; however, DNA sequences that flank the 5' end and the 3' end of the 3.1 kb fragment are contained in the original lambda phage clones, designated lambda Maprt-11 and lambda Maprt-12, and will be available if needed. As the figure indicates, the gene has at least 4 introns that interrupt the coding sequences. There may be a fifth intron in the untranslated 5' region of the gene. The cDNA does not extend to its natural 5' terminus, but is sufficient to encode 151 amino acids that represent greater than 90% of the mature protein. The size of the messenger RNA, determined by "Northern blotting," is about 1060 bp. The 5' end of the gene contains a CAAT sequence 95 bp downstream from the Eco R1 cloning site, and a TATA sequence yet another 54 bp downstream. The sequences are thought to represent part or all of the eukaryotic promoter. Additional 5' flanking sequences, however, have been implicated in the regulation of gene expression. There is a concensus CAP site 26 bp downstream from the TATA box, which is most likely the position from which transcription begins.

In one embodiment of the invention, the construction of the tester lines is presented briefly below and will be described in greater detail in the examples. For rapidly identifying mutagens, that may also be carcinogens, that induce base substitutions, a tester cell is constructed by combining DNA-mediated transformation of mammalian cells and in vitro site directed mutagenesis. From the complete DNA sequence, the specific nucleotide sequences can now be identified, which when mutated, render the gene non-functional. In accordance with the teachings of this invention, a specific transition or transversion should be introduced at one such site, for instance, a target site at an intron/exon junction, by site specific in vitro mutagenesis, thereby inactivating the gene and concomitantly destroying a diagnostic or target Pst1 restriction site. The mutated gene should then be introduced into the APRT⁻ cells by procedures such as DNA-mediated transfection or microinjection. Since a non-functional APRT⁻ gene is being inserted into APRT⁻ cells it is necessary either to contransfect with a dominant acting selectable marker, or to ligate the non-functional APRT gene to a dominant acting selectable marker prior to cotransfection or microinjection into APRT⁻ cells. Any suitable marker may be employed herewith, however, an example of a marker of choice is contained on a plasmid constructed by Southern, P. J., and Berg, P.: *J. Mol. and Applied Genetics*, 1 (4): 327-341, (1982) designated pSV3-neo. This particular plasmid contains a phosphotransferase gene which confers resistance to a variety of aminoglycoside antibiotics including neomycin, kanamycin and gentamicin. Although none of these antibiotics adversely affect mammalian cells, the related drug G418 inhibits eukaryotic protein synthesis and is, thus, toxic to mammalian cells. Introduction of pSV3-neo into cultured cells confers resistance to G418, and provides a convenient selectable marker.

In carrying out the invention, a human APRT⁻ line such as HTD-114, which is non-reverting and useful for transfection, is cotransfected or microinjected with a mixture of site specific in vitro mutated APRT gene and a pSV3-neo at about a 20:1 APRT gene to pSV3-neo plasmid ratio or with multiple copies of the site specific in vitro mutated APRT gene ligated to pSV3-neo, as indicated above. These procedures preferentially increase the probability of introducing a larger number of targets for mutagenesis. Since it is an objective to locate a reversion event at a specific site, manifested as a dominant trait in the selection system, the sensitivity of the mutagenicity test can be increased ten-fold, if, for example, 10 copies of the mutated mouse APRT gene are stably integrated into the human host cell genome.

The sensitivity of the test system is advantageously within a useful range. The frequency of generating APRT⁻ cells from diploid or pseudodiploid lines after mutagenesis with, for instance, ethyl methane sulfonate (EMS) or ICR (Institute for Cancer Research) compounds is about $10^{-6}$ to $10^{-7}$. For putative heterozygotes, the frequency is about $10^{-3}$. The coding region of the APRT gene is less than 1000 bp. In considering third nucleotide redundancies or other possible silent mutations, the effective target size for inactivating a single copy of the gene is in the range of about 700 bp. The probability of mutation at a specific base pair would therefore be about $1.4 \times 10^{-6}$ ($1/700 \times 10^{-3}$), assuming (for expositional purposes) that mutational events occur at random. This calculation approximates the reversion frequency from APRT⁻ to APRT⁺ that should be observed in the human construct described above if it contained only one mutated mouse APRT gene. If, for example, ten such genes were present, the reversion frequency should be raised to about $1.4 \times 10^{-5}$.

One method for detection of frameshift mutations and mutagens entails having a series of peptides synthesized that represent frameshift peptides predicted from the DNA sequence data. As part of this approach, regions of the DNA sequence that are particularly useful have now been identified. In accordance with this method, antibodies specifically directed against the prepared frameshift peptides are prepared by any suitable known techniques, such as monoclonal antibody techniques, and used as screening reagents. For screening, APRT⁺ cells are treated with putative or known mutagens, and selected for cells with partial (APRT⁻/APRT⁺) or fully (APRT⁻/APRT⁻) adenine analog-resistant phenotypes by culturing in medium containing, for example, 2,6-diaminopurine (DAP), 2-fluoroadenine (FA) or 8-azaadenine. This procedure alone will provide information regarding the mutagenicity of the compound being tested. To determine whether or not any of the fully or partially drug resistant cell colonies results from a frameshift mutation, they can be examined for peptides reacting with, for instance, anti-frameshift immunoglobulin(s). Thus, it is possible to analyze colonies directly on the dish in which they arose using a second iodinated or chromagen-coupled antibody, a labeled antibody, or a labeled Staphylococcus protein A, and to determine what faction of fully or partially drug resistant colonies are due to a frameshift mutation. As an alternative approach, a frameshift mutation is constructed by inserting an extra nucleotide or deleting a nucleotide in the region of the gene encoding the amino terminal end of the protein. Mutagens that produce frameshifts by point deletions or insertions can be detected by reverting the tester cells to the APRT⁺ phenotype. The mutagen induced point deletion or insertion can be at the site of the engineered insertion or deletion, respectively, or may occur at a second site that completely or partially restores APRT activity.

Detection of mutations due to transposition or excision of transposable elements entails construction of a cell line, heterozygous or hemizygous for a selectable gene, such as APRT, in which the functional selectable gene is inactivated by insertion of a retrovirus proviral DNA within or adjacent to the selectable gene. Detection of compounds or agents that cause mutations by facilitating or promoting transposition or excision of mobile DNA elements entails incubating said negative cells with agents to be tested for a sufficient time to allow mutation to occur, and incubating said cells in culture medium that selects for cells with a positive phenotype. Confirmation that reversion to the positive phenotype is due to transposition or loss of the proviral DNA could be accomplished by conventional "Southern blotting."

Figure 4:
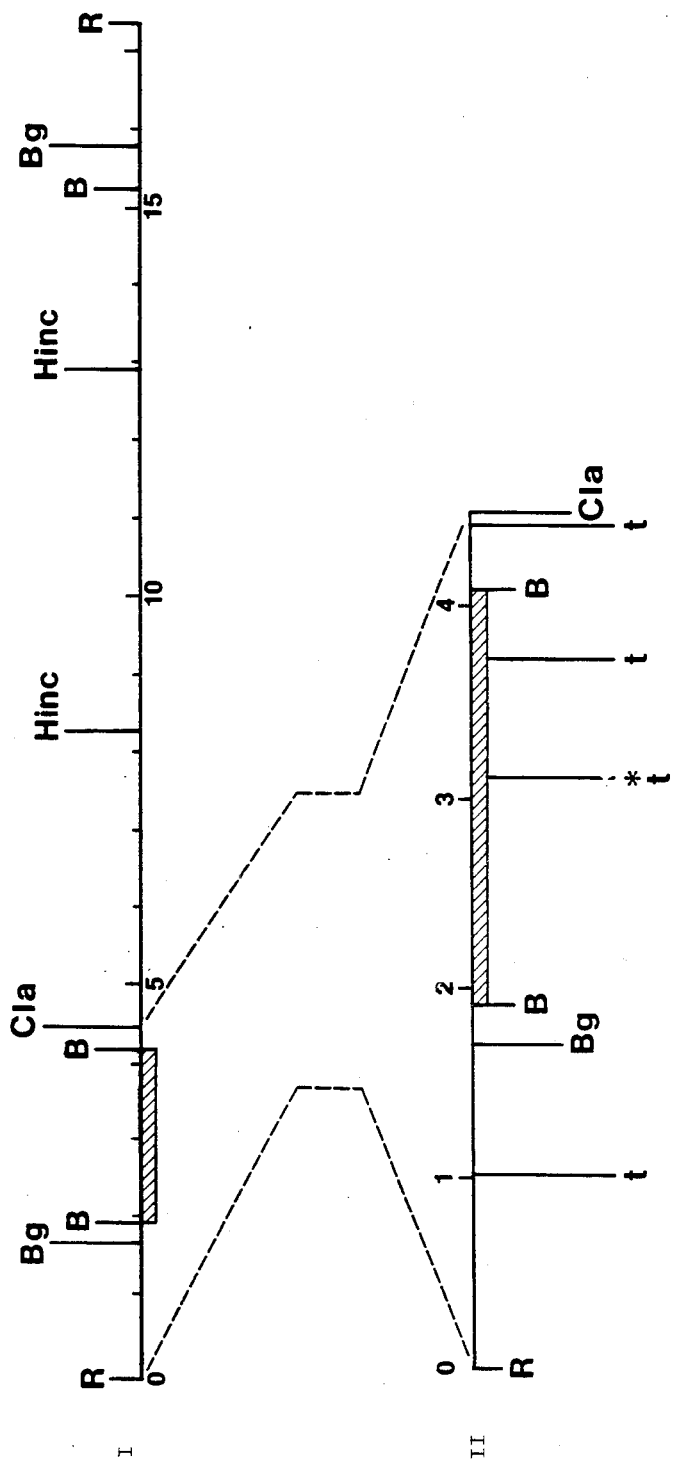
FIG. 4 is a restriction map of functional human APRT gene and flanking sequences.

Identifying mutagens that produce extensive deletions or rearrangements not due to transposition of a specific transposable element is also in accord with the methodology of this invention. Such methodology is slightly more time consuming. It is still possible to quickly know whether or not a given mutagen induces base substitutions, frameshifts or specific transpositions in mammalian cells. If the mutagen falls into none of these categories, it should be tested to determine if it induces major genomic rearrangements or deletions. Since the mouse APRT gene is now cloned, this can readily be done by, for example, conventional "Southern blotting" methods. In addition, the human APRT gene has also been cloned and partially characterized, thus, this assay can also be applied to human HT-1080 cells, for example, for consistency. A partial restriction map of the cloned human APRT gene and its flanking DNA sequences is presented in FIG. 4. As part of this method, the genomic DNA from mutagen-induced APRT⁻ cells can be digested with any of several known diagnostic restriction enzymes, such as, HindII, BamH1 or PvuII, size fractionated by agarose gel electrophoresis blotted onto nitrocellulose, and hybridized with $^{32}$P-labeled APRT DNA. If deletions or rearrangements have occurred, they will be accompanied by labeled restriction patterns that differ from those of control cells digested with the same enzymes.

Many compounds, particularly polycyclic hydrocarbons, require activation by microsomal monooxygenases to become mutagenic. These monooxygenases, several of which have been purified comprise the P-450 system. One of its functions appears to be the conversion of compounds like polycyclic hydrocarbons to water soluble metabolites which can be excreted. Unfortunately, some of these metabolites can also be mutagenic and carcinogenic. Although cells of most tissues possess a related monooxygenase system referred to as P-448, the P-450 system is tissue specific and found predominantly in the liver. Since neither bacteria nor most mammalian cell lines metabolize polycyclic hydrocarbons to their highly mutagenic derivatives, investigators have resorted to prior activation by incubation with a 9000×g supernatant (S-9) of rat liver plus NADP, glucose-6-phosphate, and sodium phosphate, or to using a cell-mediated assay originally devised by Huberman, E. and Sachs, L.: *Int. J. Cancer*, 13: 326-333, (1977). In one modification of the latter protocol, cells which lack activating oxygenases are plated over or co-cultivated with lethally irradiated BHK21 feeder cells which retain activating function. Presumably, the mutagenic metabolites are produced by the feeder cells and taken up by the target cells which are then subjected to selection for appropriate drug resistance. Other cells, such as human epithelial cells have been developed as metabolizing agents for a variety of target cells.

Because the mixed cell assay is presently more cumbersome and possibly less sensitive than is desirable, it is preferred to use a single human cell line that is diploid or pseudodiploid and that has retained many liver cell functions. Thus, even though it is preferable to have mutagen activation and mutagenesis of an introduced APRT gene within the same cell, it is possible to use a transfected human APRT− cell line (e.g., HTD-114) and lethally irradiated mutagen activating cells and the introduced, non-functional, engineered gene encoding the selectable marker APRT as the target site for mutagenicity.

EXAMPLE 1

1. Construction of a Mutant Mouse APRT Gene Containing a Specific Base-Substitution The cloned mouse APRT gene, contained within a 3.1 kb fragment of mouse genomic DNA inserted into the bacterial plasmid pBR328, is designated pSAM-1. As described earlier, this gene has been sequenced in its entirety, and contains at least four and possibly five introns. The nucleotide sequence at one of the intron/exon junctions is the target for mutagenesis. The sequence surrounding and including the target site is 5' TTCCTGTCTGCAG/GCTGAG 3', and contains a Pst 1 restriction site (indicated by dashed line above sequence). The slash mark denotes the precise RNA splice site. The AG/G sequence that forms the splice site is requisite for splicing in all mammalian systems so far studied. These three nucleotides are highly conserved at intron/exon junctions and form part of a larger but less well-conserved consensus sequence. Alteration or deletion of one of these nucleotides inhibits splice formation at that site resulting in aberrant splicing and loss of functional protein encoded by that gene. As part of this method, the G, for example, that immediately precedes the splice point is converted to an A (transition) or a T or a C (transversions). Likewise, the preceding A (2 nucleotides 5' to the splice site) is converted to a G. The resulting transition or transversions have two effects. First of all, they interfere with RNA splicing, thereby blocking production of functional APRT. Secondly, they cause the loss of the Pst 1 site which serves as a useful diagnostic landmark. Regeneration of the Pst 1 by reversion site restores gene function an the APRT+ phenotype.

The preferred method which produces a targeted base substitution mutation in accordance with this invention closely follows the procedure described in Wallace et al. Walker, R. B. et al: *NUcleic Acid Research*, 9(15): 3647-3656, (1981); Zarucki-Schulz, T. et al: *J. Biol. Chem.*, 257(18): 11070-11077, (Sept. 1982). Nevertheless, other known suitable methods can also be employed herewith. The recombinant plasmid pSAM-1, which contains the intact APRT gene, is first made single stranded. Covalently closed circular pSAM-1 DNA is incubated with EcoRI in the presence of 150 μg/ml ethidium bromide. Under these conditions, the superhelical DNA is only nicked in one strand at the EcoRI site and becomes relaxed with greater than 95% efficiency. After removal of the ethidium bromide by isoamyl alcohol extraction, the DNA is deproteinized by phenol extraction, ethanol precipitated and fractionated on an alkaline sucrose gradient to recover single-stranded circular DNA. The sample is neutralized, ethanol precipitated, and treated with *E. coli* exonuclease III to hydrolyze any contaminating single-stranded linear molecules. The remaining circular single-stranded pSAM-1 DNA serves as the template for producing the mutant gene.

The nucleotide sequence at the intron/exon junction is 5' —CTGCAG/GCT— 3' and is mutated to 5' —CTGCAA/GCT— 3' or 5' —CTGCGG/GCT— 3' or 5' —CTGCATGCT— 3' or 5' —CTGCAC/GCT— 3'CTGCAG/ACT, or CTGCAG/CCT or CTGCAG/TCT to produce the desired transitions or transversions. To this end, the following octadeconucleotides 5'TCCTGTCTGCAA/GCTGAG3', 5'TCCTGTCTGCGG/GCTGAG3', 5'TCCTGTCTGCAT/GCTGAG3', 5'TCCTGTCTGCAC/GCTGAG3', 5'TCCTGTCTGCAG/ACT3', 5'TCCTGTCTGAAG/CCT3' and 5'TCCTGTCTGAA/TCT3' are synthesized. Each of these oligonucleotides are complementary to the strand not shown at the splice region of interest except at the underlined nucleotide, which is the mutated site.

As an example, the oligonucleotides 5'TCCTGTCTGCAA/GCTGAG3' and 5'TCCTGTCTGCGG/GCTGA3' are phosphorylated at their 5' ends with T4 polynucleotide kinase, and hybridized with closed circular single-stranded pSAM-1 DNA. The hybridized oligonucleotide serves as a primer which is extended upon addition of *E. coli* DNA polymerase 1 (Klenow fragment), the four deoxynucleotide triphophosphates and ATP. The reaction mixture, which also includes T4 DNA Ligase, is incubated at 12° for 12 hours. The product contains required circular double-stranded pSAM-1 DNA that has a C:A mismatch in the one case and a G:T mismatch in the second case at the respective target sites.

The repaired plsmid DNA is used to transform *E. coli* MC 1061 by conventional procedures. Transformants are selected preferably by their resistance to ampicillin. In principle, 50% of the transformants carry the normal APRT gene and 50% the mutated gene. Further, techniques such as identification of transformants containing the mutant gene include, for instance, the known presence of colony hybridization. Using mutant oligonucleotide as a hybridization probe after 5' end-labeling with γ-[$^{32}$P] ATP and T4 polynucleotide kinase, it is possible to distinguish colonies containing mutant DNA complementary to the entire length of the hybridization probe from colonies that contain non-mutated DNA.

Transformant colonies grown on nitrocellulose filters are replica plated on nitrocellulose filters. Colonies on replica filters are prepared for hybridization with the [$^{32}$P] end-labeled octadecanucleotide that is used to produce the desired base substitution. The hybridization conditions, which are nonstringent, entail incubation for 16 hours at 55° C. in 6×NET (1×NET=150 mM NaCl, 1 mM EDTA, 15 mM Tris-HCl pH 7.5) containing 5X Denhardt's solution, 10% dextran sulfate, 250

µg/ml yeast tRNA, 0.5% nonidet NP-40 and 2 ng/ml radioactive probe. The filters are washed at 0° C. in four to six changes with 6×SSC (1×SSC=0.15M NaCl, 0.015M Na citrate, pH 7.2), dried and exposed to XR-5 x-ray film and intensifing screen at −70° for 12 hours.

Colonies hybridizing with the probe are recovered from the master filter, expanded, and plasmid DNA prepared by conventional means. Since a colony can conceivably contain plasmids with both wild-type and mutant APRT DNA, this possibility is examined by digestion with Pst 1. The parental plasmid pSAM-1 has two Pst 1 sites, one in the vector and the second at the target splice junction. Digestion with Pst 1 generates two fragments, 2.7 kb and 3.5 kb in length. Plasmid containing mutant APRT DNA lacks the second site and yields only the linear 6.2 kb fragment upon Pst 1 digestion. Should colonies contain a mixture of wild-type and mutant plasmid DNAs, a second round of transformation with isolated plasmid DNA and re-screening of colonies should be performed as above to separate parental from mutant plasmids. As a final precaution, the nucleotide sequence containing the targeted site of the mutated gene is determined to ensure that only the desired mutation is introduced.

2. Introduction of mutant muse DNA into human APRT− cells

A plasmid containing mutant APRT DNA with an engineered transition is introduced, for example, into HTD-114 cells, an APRT− derivative of the human fibrosarcoma cell line HT1080, by DNA-mediated transfection using the Ca++ DNA phosphate precipitate method, as modified by Wigler et al. Wigler, M. et al: *Proc. Natl. Acad. Sci. USA*, 76(3): 1373–1376, (March 1979) or by microinjection. Since there is no way to select for APRT− cells that have taken up a mutant APRT gene, mutant genes are introduced either by cotransfection with a dominant selectable marker or after ligation to a dominant selectable marker, or by microinjection with a dominant selectable marker. As briefly described above, the plasmid pSV3-neo was used to confer resistance to the drug G418. For example, site-specific in vitro mutated pSAM-1 is mixed at about a 20:1 ratio with pSV3-neo. Aliquots of this mixture containing 50 ng of plasmid plus 20 µg carrier APRT− DNA are used for transfection of $2.5 \times 10^5$ cells per 100 mm culture dish. One ml of DNA precipitate is added to 10 ml of medium in each flask and incubated for 6 hours. The medium is then replaced with fresh non-selective (drug-free) medium for an additional 24 hours. Selection medium containing 200 µg/ml G418 is then added to the cells and replaced every 3 days. Colonies resistant to the drug are then isolated and grown for subsequent testing. Alternatively, mutant pSAM-1 is ligated to the neo-containing DNA and the product used for transfection as above.

To determine which of the selected colonies contains the mutant mouse APRT gene, DNA from each of several colonies is isolated, digested with Pst 1 as well as other restriction enzymes, fractionated by agarose gel electrophoresis, and subjected to "Southern" blotting, using $^{32}$P-labeled mouse APRT DNA as a probe. Since the mouse APRT DNA probe does not cross-hybridize with the human APRT gene under stringent conditions, only those colonies that take up the mouse gene yield a radioactive signal. Furthermore, the mutant genes lack the internal Pst 1 site which is regenerated and serves as a diagnostic marker when the gene is reverted to its functional state. Because the introduced mutation is at an RNA splice junction, reversion by second site mutation is unlikely. As further verification that the product of the mutant mouse gene was non-functional, (the cells are still APRT−), the cells now grow in medium containing 2,6-diaminopurine (DAP) or fluoroadenine (FA), but are killed by AAA medium containing adenine plus azaserine and alanosine (which blocks de novo AMP biosynthesis). Since in co-transformation experiments 90% or more of selected colonies take up other foreign DNAs presented to them, the majority of the colonies selected contain one or more copies of the mutant APRT gene. The "Southern" blot analysis, after combined restriction digestion with EcoR1 and Sph1, verifies that the cloned EcoR1/Sph1 fragment remains intact in the transfected cell. This blot analysis not only confirms the presence of the mutant APRT gene in the recipient cell but provides an estimate of its copy number. Transfectants with a copy number of 10 or greater are chosen and grown in the presence of G418 and DAP. Copy number is estimated by comparison with hybridization with a β-globin probe.

The stability of the transfectant cell line, i.e., the retention of intact multiple mutant APRT genes, is periodically assessed. When DNA is taken up by cells, it is concatenated into large linear structures which become randomly integrated into one of the host cell chromosomes. The mutant APRT genes generally remain closely linked to PSV3-neo DNA, and are usually retained so long as G418 resistance is maintained. After many cell generations, the mutant APRT genes become stable components of the recipient cell genome, even in the absence of selective pressure. To identify cells with multiple, stable integrated mutant mouse APRT genes, transfected cells are maintained in the presence of G418 and also transferred to non-selective (drug-free) medium for several passages. Then, the cells from non-selective medium are replated at low density in medium containing G418 and their plating efficiencies compared to that in non-selective medium. Equal plating efficiencies in both media indicates the stable integration of the pSV3-neo marker. Individual clones that arise in selective medium are grown and examined by "Southern" blot analysis to determine mutant APRT gene copy number. Clones with high copy number are retained and subjected to a second and possibly subsequent rounds of stability testing and selection. In this manner, it is possible to identify a clone(s) which has integrated multiple mutant APRT genes in a stable fashion so that no further selection is required for their retention. As discussed above, having multiple mutant APRT genes proportionally increases the target size and thereby the sensitivity of the system for detecting mutagens. Thus, cells are periodically passaged in medium containing DAP to ensure that none of the mutant APRT genes have undergone a spontaneous reverse transition at a specific previously altered site to become functional.

3. Detection of mutagens that produce transitions

The tester human cell lines described above, containing multiple copies of one or the other specifically mutated mouse APRT genes, serve as an indicator for mutagens that primarily produce transitions. To verify the system, ethyl methanesulfonate (EMS), a potent alkylating agent and mutagen that causes G:C→A:T transitions in bacterial cells, and 2-aminopurine, which produces transitions with a preference for A:T→G:C in bacterial and mammalian cells, are applied. Appropriate concentrations of each agent are chosen after establishing a cell killing curve. Bracketing concentrations are also tested. The mean lethal dose ($D_o$) is calculated for comparison of mutagenic potencies. After exposure to mutagen, cells are placed in AAA medium to select for APRT+ colonies. These colonies arise as a consequence of a G:C→A:T transition in the former case and a A:T→G:C transition in the latter. In both cases, the mutation occurs at the specific in vitro mutated site within one of the mutant mouse genes so that a functional intron/exon splice junction is restored, allowing mRNA splicing and production of active enzyme. Starch gel electrophoresis permits the unambiguous demonstration of the mouse gene origin of the APRT expressed. If necessary, immunologic methods can also be used.

It should be noted again that the scheme conducted above represents a model system, and that both possible transversions can also be engineered at precisely the same nucleotides by the same methods and with the same result (i.e., inactivation of the gene by disruption of the splice site). Furthermore, the procedure is not restricted to mutagenesis by compounds like 2-aminopurine or EMS, but can be extended to mutagenesis by mutagens such as compounds, radiation, gamma rays, electron beams and substances that require activation by liver microsome preparations.

EXAMPLE 2

Detection of frameshift mutagens and mutagens

Antibodies are produced to frameshift peptides of APRT as a diagnostic tool for identifying mutagens andd potential carcinogens that induce frameshift mutations. The strategy is dependent upon knowing the nucleotide sequence of the cDNA encoding mouse APRT. As stated earlier, the nucleotide sequence of the entire mouse APRT gene, and of a cDNA has been determined. From this information, the amino acid sequence of 152 amino acids from the carboxy terminal end of wild type APRT was deduced. Based upon the position of putative splice sites at the 5' end of the gene, and their proximity to a translation initiation site, it is believed that the sequence of the remaining 8 amino terminal acids is known. Uncertainty of these terminal amino acids in no way interferes with the protocol. For reference, the mouse APRT cDNA nucleotide sequence and the amino acid sequence that it encodes are presented in FIG. 2.

Introduction of a point deletion in the gene at a site corresponding to the amino terminal region of the protein results in a reading frame containing 9 chain termination codons. These occur at nucleotide positions 16, 67, 109, 142, 379, 394, 403, 421 and 502. Three peptides representing frameshift sequences produced by point deletions are synthesized for use as immunogens. These peptides are encoded by nucleotides that extend from positions 19 to 66, 319 to 378 which terminate an open reading frame beginning at nucleotide 149, and 451 to 501 which terminates an open reading from beginning at nucleotide 424 and which reads through the normal translation termination site to introduce an additional 14 amino acids. The frameshift peptides synthesized from the sequences described above are presented below. The underlined amino acids at the amino- or carboxy-terminal ends to not appear in the frameshift peptides but are included to permit coupling to carrier protein (in the case of cysteine) or facilitate iodination (in the case of tyrosine).

(1) $H_2N$ cys lys thr arg thr pro ser glu leu pro ser ala ser try pro val thr tyr $CO_2H$
(2) $H_2N$ tyr glu pro cys leu arg pro val thr cys cys thr ser ser gly leu phe trp trp ser val $CO_2H$
(3) $H_2N$ try ser met thr glu glu leu ala arg trp ser his pro cys ser gln gln his $CO_2H$ The first peptide represents the complete nonsense amino acid sequence encoded by a short open reading frame near the 5' end of the cDNA. The second peptide contains only the terminal 20 amino acids of a long open reading frame encoding a nonsense peptide comprised of 78 amino acids. The third peptide contains the carboxy terminal 17 amino acids of a frameshift peptide that is comprised of 26 amino acids and that extends beyond the normal translation termination signal.

Introduction of a point insertion (or 2 nucleotide deletion) at the 5' end of the coding region produces 5 open reading frames punctuated by stop signals. Beginning from the 5' end, the open reading frames terminate at nucleotides 241, 298, 337, 361 and 454. The frameshift peptides which are produced by a single nucleotide insertion, and which serve as immunogens, are as follows:

(1) $H_2N$ tyr glu ala ala gly pro his cys val ser leu leu phe ser gly val try glu gly $CO_2H$
(2) $H_2N$ tyr ala gly asn pro glu arg cys leu gly thr arg ala glu ser gly his cys gly $CO_2H$
(3) $H_2N$ cys ala arg thr tyr thr ile leu leu ser pro pro val $CO_2H$ The first peptide contains the terminal 18 residues of an 80 amino acid peptide terminating at nucleotide 241. The second is the terminal octadecapeptide of a frameshift protein encoded by the nucleotide sequence extending from position 245 to 298. The third is a dodecaptide representing the amino terminal end of a 30 amino acid frameshift peptide that terminates 2 nucleotides upstream from the normal termination site.

Short peptides, especially those that contain hydrophilic residues, are sufficient to elicit antisera capable of reacting with the intact frameshift proteins from which the peptides are derived. Peptides that contain one or more proline residues are particularly effective in producing an antibody response. Since the peptides selected all have hydrophilic regions and at least one proline residue, they serve as effective immunogens. These peptides were chosen since antibodies they elicit react with frameshift proteins encoded by various segments of the gene. These antibodies therefore detect not only full length +1 and +2 frameshift proteins, but also those that terminate prematurely.

To increase the immunogenicity of the synthetic peptides, they are coupled to a carrier protein. Although several coupling procedures have been developed, the procedure utilized is the one described by Sutcliffe et al. Sutcliffe, J. G. et al: Science, 219: 660–665, (February 1983) and by Green, N. et al: Cell, 28: 477–487, (March 1982). In this approach, the carrier protein, keyhole limpet hemocyanin (KLH) is coupled with each of the synthetic peptides via cysteine sulfhydryl goups. This procedure is very mild and avoids self-coupling of the peptides. For the two synthetic peptides that lack a cysteine residue, a cystine at their amino termini is included. Also, an amino (or carboxy) terminal tyrosine is appended to each of the peptides to provide a substrate for iodination. An aliquot of iodinated peptide is used as a control to monitor the extent of coupling to the carrier protein. The addition of a terminal cysteine or tyrosine to synthetic peptides affects neither their immunogenicity nor the specificity of the antibodies that they elicit.

The KLH is reacted with m-maleimidobenzoyl-N-hydroxysuccinimide ester (MBS) from Sigma dissolved in N,N'-dimethylformamide. The activated protein is separated from unreacted MBS by Sephadex G-25 column chromatography and is mixed with synthetic peptide in 0.1M potassium phosphate, pH 7.3, 5 mM EDTA and the pH adjusted to 6.5. After stirring for 4 hours at room temperature, the mixture is chromatographed on Sephadex G-100 and the recovered conjugated protein is used directly to immunize 3 rabbits for each peptide. The immunization schedule, which closely follows that described in Green N. et al: *Cell*, 28: 477–487, (March 1982) entails two successive subcutaneous injections with 200 μg of peptide-coupled KLH with adjuvant, and a third intraperitoneal injection with alum-precipitated antigen over a three week period. The rabbits are boosted with antigen precipitated on alum at five week intervals. Antibody titers are monitored by double immunodiffusion.

The antisera elicited are tested for their reactivity with each of the frameshift peptides and with purified native mouse APRT using an enzyme-linked immunoabsorbent assay (ELISA). Antigen (5 pmol) in phosphate buffered saline (PBS) containing 0.1% bovine serum albumin (BSA) is added to wells of a microtiter plate, dried overnight at 37° C. and fixed with 50 μl methanol per well for 5 minutes at room temperature. To block non-specific adsorption, wells are coated with 3% BSA in PBS for 4 hours. Serial dilutions (1:2) of each antiserum (25 μl aliquots) are added to each well and the plates are incubated overnight. After removing unbound antibody and washing the wells with water, the bound antigen-antibody complex is reacted with a 25 μl aliquot of goat anti-rabbit IgG coupled to glucose oxidase. Excess anti-rabbit antibody is removed by thorough washing with water and color development is initiated by addition of 50 μl per well of developing solution containing glucose, horseradish peroxidase, and chromogen [2,2' azino-di-(3 athylbenzthiazolin sulfonate)] from Sigma.

Each of the antisera reacts with the synthetic peptide used as the immunogen. However, it is also important to verify that these antisera react with larger frameshift peptides. Based on unpublished data that antibody to synthetic peptides has been used to detect viral frameshift proteins, it is anticipated that they will. As a test system, an APRT gene with a single nucleotide insertion or deletion introduced at defined sites by in vitro mutagenesis is constructed. As an example, the first mutation prepared involves inserting a G between positions 90 and 91 of the cDNA sequence. The method is analogous to that described by Gillam, S. et al: *Gene*, 12: 129–137, (1980) to introduce a defined nucleotide deletion into ϕX174 and is essentially the same as the nucleotide extension method described for producing base substitutions described above. The synthetic oligonucleotide is complementary to a defined region of the gene except that a single nucleotide is deleted or added. The recombinant plasmid is rendered single-stranded as described earlier, and the oligonucleotide hybridized with the plasmid and extended with *E. coli* PolI (Klenow) to produce the heteroduplex containing the single nucleotide deletion loop. The repaired plasmid used to transform *E. coli* strain MC1061 and transformants are selected by their ampicillin resistance.

Transformants carrying the mutant gene are identified by isolating DNA from mini plasmid preparations and by digesting with SalI. The parental plasmid, pSAM-1, has a single SalI site located in the vector and is linearized by that enzyme. Insertion of a G between nucleotides 90 and 91 creates a new SalI site as well as produces a frameshift mutation. The plasmid yields two fragments, 1.9 kb and 4.3 kb in size, after SalI digestion. The frameshift sequence produces a peptide of at least 80 amino acids, prematurely terminating at nucleotide 241 of the cDNA sequence. The terminal 51 amino acids represents nonsense protein and reacts with the appropriate antiserum. It is recognized that such a mutant gene could be used in a reversion assay; however, the immunological approach should prove more sensitive.

To test the efficacy of antisera for detection of frameshift peptides in cultured cells, human HTD114 APRT⁻ cells are cotransfected with the mutated APRT gene and the neomycin resistance marker, and cells selected in the presence of G418. Transfectant colonies are tested for the presence of the mutated APRT gene by Southern blot hybridization after SalI digestion, and colonies that contain the gene are expanded for further analysis. As one approach, supernatants of cell lysates from wild-type and transfected cells are electrophoresed via SDS-PAGE and the resultant gels blotted or electroblotted ("Western" blots) to nitrocellulose sheets. These sheets are then incubated with antibody against mouse APRT (which we have) or frameshift peptide. Antibody bound to APRT or frameshift peptide is then localized with $^{125}$I-Staphylococcus protein A or a second antibody conjugated to peroxidase. The antibody against frameshift peptide elucidates a band representative of a truncated protein with a molecular weight between 8000 and 9000 daltons. It has been determined that antibody against wild-type APRT elucidates a protein band of about 17,500 daltons.

Since the above immunological assay would be too cumbersome to carry out routinely on a large number of colonies, a rapid in situ test is developed. As a model system, the human cell transfectant carrying the mutated mouse APRT gene is used with a frameshift mutation. These cells are plated at low density to yield about 100 colonies per 100 mm dish. Wild type APRT⁺ human and mouse cells are plated in separate dishes as controls. The colonies are fixed by incubation with 4% formaldehyde in phosphate buffered saline (PBS) for 20 minutes at room temperature, rinsed with PBS and treated with cold (−10° C.) methanol for 10 minutes to permeabilize the cells. The plates are overlayed with a 3% BSA solution in PBS for 4 hours to block non-specific antibody binding sites, and after removal of BSA are incubated for 1 hour at 37° with diluted anti-frameshift antibody. The plates are washed with PBS, incubated with goat anti-rabbit IgG, washed again with PBS to remove unreacted IgG, and incubated with iodinated protein A. Positive colonies, detected by autoradiography, are evident in plates containing mutant transfected cells but not in those containing wild type cells.

As an alternative and equally sensitive method, a peroxidase-coupled chromagen technique is developed to detect positive colonies. A significant advantage of such an approach for large scale usage is that the assay avoids the use of radioactivity and produces more rapid results. The method is essentially the same as that described above but with a few modifications. For example, endogenous peroxidase activity is eliminated by incubation with 0.03% hydrogen peroxide in PBS after formaldehyde and methanol fixation. The cells are extensively washed to remove the peroxide. The plates are overlayed with 3% BSA in PBS and, after further washing, incubated with the appropriate rabbit antiserum as above. The antiserum is removed, and the plates incubated for 45 minutes at 37° C. with goat anti-rabbit IgG conjugated with horseradish peroxidase. The plates are washed and chromogen and hydrogen peroxide (0.01%) added. Useful chromagens include 3-amino-9 ethylcarbazole (Sigma), 4 chloro-1-napthol (Sigma), and 3,3' diaminobenzidine tetrachloride dihydrate (Aldrich).

EXAMPLE 3

Mouse cells that are hemizygous or heterozygous at the APRT locus are superinfected with Maloney Murine leukemia virus, a well characterized retrovirus (RNA tumor virus). Cells that are rendered APRT− are selected in medium containing DAP or FA. To demonstrate that the cells are negative due to insertion of proviral DNA within or adjacent to the functional APRT gene, DNAs from each of several APRT− cell lines are analyzed for altered restriction patterns by Southern blotting, using cloned APRT DNA as a probe.

Cells which have proviral DNA inserted adjacent to the APRT gene or within an APRT intron serve as potential tester lines for mutagens that facilitate transposition of mobile elements. Said cell lines are incubated with a mutagenic substance for sufficient time to permit mutagenesis. Cells are placed in AAA medium to select for those cells that are rendered APRT+ by said mutagen. The DNAs from such cells are tested by Southern blot analysis to confirm that mutation to the APRT+ phenotype is due to transposition or loss of proviral DNA associated with APRT Locus.

EXAMPLE 4

Detection of DNA rearrangements

Some mutagens which produce mutations at the APRT locus (i.e., confer an APRT− phenotype upon APRT+ cells) exert their effect by inducing DNA rearrangements rather than by introducing base substitutions or small frameshift mutations. Agents that generate APRT− cells, but which are not detected by any of the abov tester cell lines, are considered candidates for mutagens that cause DNA rearrangements including large nucleotide deletions, translocations, inversions, etc. To test for such rearrangements, cells rendered APRT− by these mutagens are examined by Southern blot analysis. The internal restriction pattern of the wild type APRT gene (see FIG. 1) and of the regions flanking the gene (FIG. 3) have been determined. Furthermore, from nucleotide sequence data, the restriction sites for more than an additional 75 enzymes are known. Restriction enzyme digestion with any one of several enzymes (e.g., HindIII, BamHl or PvuII) followed by Southern blot analysis using the cloned gene or fragments thereof quickly indicates whether a substantial deletion or DNA rearrangements has occurred and where within this locus the lesion is localized.

A current alternative to the APRT mouse gene is the human APRT gene which has been cloned in accordance with the following procedures.

a. Cell Culture: Mouse APRT− L cells, designated LS-24b (Tischfield, J. A. et al: *Mol. Cell. Biology*, 2(3): 250–257, (May 1982) were maintained in modified Eagels medium (MEM) supplemented with 5% calf serum, 5% fetal calf serum and non-essential amino acids. Selective medium (AAA medium) for APRT+ cells contained 0.05 mM azaserine, 4 μg/ml alanosine, and 0.1 mM adenine (Tischfield, J. A. et al: *Mol. Cell. Biology*, 2(3): 250–257, (May 1982).

b. Library Screening: A human APRT gene was retrieved from a Charon 4A lambda phage human genomic library, maintained in *E. coli* DP50 supF, and kindly provided by Maniatis, T. et al: *Cell*, 15: 687–701, (Oct. 1978). The library was screened as described by Benton and Davis Benton, W. D. and Davis, R. W.: *Science*, 196(8): 180–182, (April 1977), using a mouse APRT DNA probe, whose isolation we have previously reported Sikela, J. M. et al: *Gene*, 22: 219–228, (1983). Because mouse APRT DNA does not detectably cross hybridize with the human APRT gene in genomic Southern blots (not shown), even under non-stringent conditions ($3 \times$ SSC, 57° C.), the screening was performed under non-stringent conditions. The probe was a 1 kb Bam H1 fragment containing much of the mouse APRT coding region subcloned into phage M13mp10 DNA. The probe was labeled by nick-translation see Rigby, P. W. J. et al: *J. Mol. Biol.*, 113: 237–251, (1977), and hybridized with recombinant phage DNA on replica filters for 24 h at 57° C. in $10 \times$ Denhardt's solution, see Denhardt, D. T.: *Biochem. Biophys. Research Comm.*, 23(5): 641–646, (1966), and $3 \times$ SSC ($1 \times$ SSC=0.015M Na citrate, 0.15 m NaCl).

c. Phage-mediated Transfection: Putative recombinant phage containing human APRT DNA were plaque purified and propagated in *E. coli* LE 392. Each clone was individually tested for the presence of a functional APRT gene by a phage-mediated transfection assay, see Sikela, J. M. et al: *Gene*, 22: 219–228, (1983) and Ishiura, M. et al: *Mol. Cell. Biology*, 2(6): 607–616, (June 1982), using the LS-24b cell line, see Tischfield, J. A. et al: *Mol. Cell. Biology*, 2(3): 250–257, (May 1982), as a recipient. One ml of calcium phosphate precipitate containing $5-20 \times 10^8$ plaque purified phage was added to $5 \times 10^5$ recipient cells in a 75 cm$^2$ flask containing 10 ml of non-selective medium, see Ishiura, M. et al: *Mol. Cell. Biology*, 2(3): 607–616, (June 1982). After 24 h, medium containing the precipitate was aspirated and replaced with MEM. After another 24 h, the MEM was replaced by selective AAA medium. Macroscopic colonies were visible after 2 weeks, and individual colonies were picked and expanded.

d. Preparation of DNAs, Restriction Enzyme Digestion and Blot Hybridization: Bacteriophage and plasmid DNAs were prepared by conventional methods as described in Maniatis, T. et al: Isolation of Bacteriophage λ and Plasmid DNA, In: *Molecular Cloning. A Laboratory Manual*, Cold Spring Harbor Laboratory pp. 80–97, (1982). Preparation of genomic DNA was as previously described in Stambrook, P. J.: *J. Mol. Biol.* 82: 303–313, (1974). Conditions for restriction enzyme digestion of genomic or cloned DNAs were those recommended by the supplier, Bethesda Research Laboratories. Digested DNAs were electrophoresed on 1% agarose gels and blotted as described in Southern, E. M.: *J. Mol. Biol.* 98: 503–517, (1975) to Gene Screen Plus (New England Nuclear). The filters were hybridized at 65° C. with a $^{32}P$-labelled, 2.1 kb Bam H1 fragment of the human gene (see below) in 1% sodium dodecyl sulfate, 1M sodium chloride 10% dextran sulfate and 100 μg/ml denatured salmon sperm DNA. Filters were washed according to the supplier's recommendations except for the final wash which was at 65° Cl for 45 m in 0.1×SSC and 1% sodium dodecyl sulfate.

RESULTS

Mouse APRT DNA was used to screen a human genomic lambda library. Of $2\times10^5$ individual plaques screened, the DNA from 2 plaques hybridized with the probe. Of 3 isolates tested, only one (designated λHuap15) had the capacity to confer an APRT+ phenotype upon APRT− recipient mouse cells after phage-mediated transfection. Transfection efficiency ranged between $2.4-2.8\times10^2$ transfectants per μg DNA (assuming $1\times10^9$ phage particles contain about 50 ng of DNA). The APRT activities of five transfectant clones were similar to that of wild-type mouse and human permanent cell lines. Confirmation that the cloned APRT genes is of human origin was obtained by starch gel electrophoresis of cell extracts from APRT+ transfectant colonies as previously described in Tischfield, J. A. et al: *Mol. Cell. Biology*, 2(3): 250–257, (May 1982) and Tischfield, J. A. et al: *Anal. Biochem.*, 53: 545–554, (1973). Under these nondenaturing conditions human APRT migrates more rapidly than that of mouse. All colonies arising in AAA medium following transfection with λHuap15 expressed only human APRT.

In order to identify a λHuap15 DNA subfragment that contains the APRT gene, the DNA was digested with a series of restriction enzymes, fractionated by agarose gel electrophoresis, blotted onto nitrocellulose and hybridized with [$^{32}P$] labelled mouse APRT DNA. Digestion with Bam H1 produces 8 fragments, of which only a 2.1 kb fragment hybridizes with the mouse APRT DNA probe. Restriction endonucleases Eco R1, Hind III, Sal 1, Xba 1 and Bgl II appear not to cut within the gene, since digestion with each produces a single hybridizing fragment greater than 12 kb in size. The enzymes Pst 1 and Pvu II each produce 2 hybridizing bands at 0.9 and 2.1 kb, and 0.5 and 0.6 kb, respectively.

Although the 2.1 kb Bam H1 fragment is the only Bam H1 derived fragment to hybridize with the mouse probe, it is insufficient for transfecting APRT− LS-24b cells to an APRT+ phenotype. However, since this fragment encodes much, if not most, of the functional APRT gene, and since it contains no repetitive sequences, it has been subcloned into the Bam H1 site of phage M13mp10 DNA and used as a probe to identify restriction fragment length polymorphisms within or closely linked to the human gene. DNA samples from unrelated individuals were digested with either Eco R1, Hind III, Bam H1, Pst 1, Pvu II or Tag 1 and subjected to Southern blot analysis. While the first five enzymes revealed no DNA polymorphisms, digestion with Tag 1 detects a polymorphic site. Of 24 DNA samples digested with Taq 1 and probed with the APRT Bam H1 fragment, 17 produced 3 labelled fragments at about 550 bp, 600 bp and 2.1 kb while the remaining 7 displayed an additional band at 2.7 kb (FIG. 3). The appearance of the additional 2.7 kb band is consistent with the pattern expected for individuals heterozygous for the loss of a Tag 1 restriction site within the APRT gene.

DNAs from two APRT deficient brothers (lymphoblast lines 904 and 905 and fibroblast line 345) and an unrelated heterozygote (1411) were digested with Bam H1, Pst 1, Tag 1, Bgl II or Pvu II and blot hybridized with the above noted 2.1 kb Bam H1 probe. In all cases the fragment sizes were the same as wild-type and the more common Tag 1 pattern was observed. The same was true for three independent HT-1080 derived, APRT− cell clones (HTD-114, HDT-2 and HTD-19).

Having described the invention in the above detail, it will become apparent to one of ordinary skill that other modifications are within its scope and such may be made without departing from the invention.

What is claimed is:

1. A method of identifying a mutagenic agent which induces base substitution mutation in DNA in mammalian cells comprising the steps of
    (a) introducing a cloned gene having a DNA sequence encoding a known selectable characteristic when in an unmutated form into nonreverting mammalian cells to produce transfectants of the mammalian cells, the untransfected nonreverting mammalian cells being nonselectable for said characteristic when cultured in a cell culture selection medium and the cloned gene having a base substitution at a specific site rendering the gene or its product nonselectable for said characteristic, whereupon said introduction of the cloned gene into the nonreverting mammalian cells renders the transfectants of the mammalian cells selectable for the characteristic when cultured in the cell culture medium following base substitution mutagenic reversion in the cloned gene at the specific site,
    (b) exposing the transfected mammalian cells to a mutagenic agent for a sufficient amount of time to induce reversion by base substitution mutagenesis in the cloned gene at the specific site,
    (c) culturing the exposed transfected mammalian cells in the cell culture medium which selects for those transfected mammalian cells that are selectable for said characteristic as a result of base substitution mutagenic reversion in the cloned gene at the specific site, and
    (d) identifying the mutagenic agent which has induced the base substitution mutation at the specific site in the cloned gene in the selected transfected mammalian cells.

2. A method of claim 1 wherein the mutated clone gene encodes adenine phosphoribosyltransferase (APRT) when in an unmutated form.

3. A method of claim 2 wherein the sequence of the mutated cloned APRA gene is selected from a group of sequences consisting of a human mutated APRT gene sequence and a mouse mutated APRA gene sequence.

4. A method of claim 2 wherein the nonreverting mammalian cells cannot revert to APRT producing cells absent undergoing base substitution mutagenic reversion at the specific site in the mutated cloned APRT gene.

5. A method of claim 4 wherein the nonreverting mammalian cells are selected from a group of nonreverting mammalian cells consisting of human nonreverting mammalian cells and mouse nonreverting mammalian cells.

6. A method of claim 5 wherein the nonreverting human cells are human recessive phenotype adenine phosphoribosyltransferase (APRT−) line HTD-114 cells.

7. A method of claim 5 wherein the nonreverting mouse cells are mouse recessive phenotype adenine phosphoribosyltransferase (APRT−) LS-24b or CAK cells.

8. A method of claim 1 wherein said specific site is a Pst 1 restriction site at an intron/exon junction in a mouse gene encoding adenine phosphoribosyltransferase (APRT) when in an unmutated form.

9. A method of claim 1 including the further step of introducing a selectable marker having a DNA sequence encoding a known selectable characteristic into the mammalian cells for conferring to the transfectants of the mammalian cells an additional selectable characteristic when cultured in the cell culture medium following base substitution mutagenic reversion in the cloned gene at the specific site.

10. A method of claim 9 wherein the selectable marker is a plasmid containing a neomycin-resistance gene conferring G418 drug resistance to the transfectants of the mammalian cells as the additional selectable characteristic.

11. A method of claim 9 including the further step of introducing the selectable marker and mutated cloned gene into the mammalian cells by a method selected from a group of methods consisting of cotransfection, transfection with the mutated cloned gene ligated to the selectable marker and microinjection.

12. A method of claim 1 wherein the cell culture medium contains adenine, alanosine, azaserine or any combination thereof.

13. A method of claim 1 wherein the mutagenic agent is selected from a group of mutagenic agents consisting of a compound, radiation, gamma rays and electron beams.

14. A method of claim 1 including the further step of using in vitro site speciic mutagenesis to construct the mutated gene.

15. A method of identifying a mutagenic agent which induces frameshift mutation in DNA in mammalian cells comprising the steps of
(a) introducing a cloned gene having a DNA sequence encoding a known selectable characteristic when in an unmutated form into nonreverting mammalian cells to produce transfectants of the mammalian cells, the untransfected nonreverting mammalian cels being nonselectable for said characteristic when cultured in a cell culture selection medium and the cloned gene having a frameshift mutation at a specific site rendering the gene or its product nonselectable for said characteristic, whereupon said introduction of the cloned gene into the nonreverting mammalian cells renders the transfectants of the mammalian cells selectable for the characteristic when cultured in the cell culture medium following frameshift mutagenic reversion in the cloned gene at the specific site,
(b) exposing the transfected mammalian cells to a mutagenic agent for a sufficient amount of time to induce reversion by frameshift mutagenesis in the cloned gene at the specific selected site,
(c) culturing the exposed transfected mammalian cells in the cell culture medium which selects for those transfected mammalian cells that are selectable for said characteristic as a result of frameshift mutagenic reversion in the cloned gene at the specific site, and
(d) identifying the mutagenic agent which has induced the frameshift mutation at the specific site in the cloned gene in the selected transfected mammalian cells.

16. A method of claim 15 wherein the mutated clone gene encodes adenine phosphoribosyltransferase (APRT) when in an unmutated form.

17. A method of claim 16 wherein the sequence of the mutated clone APRT gene is selected from a group of sequences consisting of a human mutated APRT gene sequence and a mouse mutated APRT gene sequence.

18. A method of claim 16 wherein the nonreverting mammalian cells cannot revert to APRT producing cells absent undergoing mutagenic frameshift reversion at the specific site in the mutated cloned APRT gene.

19. A method of claim 15 wherein the mutagenic agent is selected from a group of mutagenic agents consisting of a compound, radiation, gamma rays and electron beams.

20. A method of claim 15 wherein the cell culture medium contains adenine, alanosine, azaserine or any combination thereof.

21. A method of claim 15 wherein the mutated cloned gene is introduced into the nonreverting mammalian cells by a method selected from a group of methods consisting of transfection and microinjection.

22. A method of claim 15 wherein the phenotypic reversion induced by the mutagenic agent results from same site or second site frameshift mutation.

23. A method of claim 15 including the further step of using in vitro site specific mutagenesis to construct the mutated gene.

24. A method of claim 15 including the further step of introducing a selectable marker having a DNA sequence encoding a known selectable characteristic into the mammalian cells for conferring to the mammalian cells an additional selectable characteristic when cultured in a cell culture medium following frameshift mutagenic reversion at the specific site.

25. A method of claim 24 wherein the selectable marker is a plasmid containing a neomycin-resistance gene conferring G418 drug resistance to the mammalian cells as the additional selectable characteristic.

26. A method of claim 18 wherein the non-reverting mammalian cells are selected from a group of nonreverting mammalian cells consisting of human nonreverting mammalian cells and mouse nonreverting mammalian cells.

27. A method of claim 26 wherein the nonreverting human cells are nonreverting human APRT⁻ line HTD-114 cells.

28. A method of claim 26 wherein the nonreverting mouse cells are nonreverting mouse APRT⁻ LS-24b or APRT⁻ CAK cells.

29. A method of identifying a mutagenic agent which induces or facilitates DNA transposition in DNA in mammalian cells comprising the steps of
(a) inserting a retrovirus proviral DNA or other transposable DNA at or near a target locus in a DNA segment of hemizygous or heterozygous mammalian cells which are selectable for a known characteristic when cultured in a cell culture selection medium, said inserting the hemizygous or heterozygous mammalian cells nonselectable for said characteristic when cultured in the cell culture medium,
(b) exposing the mammalian cells to a mutagenic agent for a sufficient amount of time to induce mutagenic reversion at or near the target locus in the DNA segment by DNA transposition, loss or excision of the proviral or other transposable DNA, (c) culturing the exposed mammalian cells in the cell culture medium which selects for those mammalian cells that are selectable for said characteristic as a result of mutagenic reversion at or near the target locus in the DNA segment, and (d) identifying the mutagenic agent which has induced the DNA mutagenic reversion at or near the target locus in the DNA segment in the selected mammalian cells.

30. A method of claim 29 wherein the DNA segment corresponds to a gene encoding adenine phosphoribosyltransferase (APRT) and the mammalian cells are hemizygous or heterozygous at or near the target locus of the gene.

31. A method of claim 29 wherein the retrovirus proviral DNA is derived from murine leukemia virus.

32. A method of claim 29 wherein the selective cell culture medium contains adenine, alanosine, azaserine or any combination thereof.

33. A method of claim 29 wherein the mutagenic agent is selected from a group of mutagenic agents consisting of a compound, radiation, gamma rays and electron beams.

34. A method of claim 29 including the further step of introducing a selectable marker having a DNA sequence encoding a known selectable characteristic into the mammalian cells for conferring to the mammalian cells an additional selectable characteristic when cultured in a cell culture medium following mutagenic reversion at the target locus in the DNA segment.

35. A method of claim 34 wherein the selectable marker is a plasmid containing a neomycin-resistant gene conferring G418 drug resistant to the mammalian cells as the additional selectable characteristic.

36. A method of identifying a mutagenic agent which induces mutation in DNA in mammalian cells and the type of mutation induced thereby comprising the step of (a) exposing mammalian cells, into which a gene having a known mutation at or near a specific site in the gene has been inserted, to a mutagenic agent for a sufficient amount of time to induce specific mutagenic DNA reversion at or near the specific site, the mutated gene having a DNA sequence encoding a known selectable characteristic when in an unmutated form, the mammalian cells being nonselectable for said characteristic when cultured in a cell culture selection medium absent undergoing mutagenic DNA reversion at or near the specific site, (b) culturing the exposed mammalian cells in the cell culture medium which selects for those exposed mammalian cells that are selectable for said characteristic as a result of specific mutagenic DNA reversion at or near the specific site, and (c) identifying the mutagenic agent which has induced the specific mutagenic DNA reversion at or near the specific site in the selected mammalian cells.

37. A method of claim 36 including the further step of using in vitro site specific mutagenesis to construct the mutated gene.

38. A method of claim 36 wherein the specific mutation is selected from a group of mutations consisting of base substitution mutation and frameshift mutation.

39. A method of claim 37 wherein the specific mutation is selected from a group of mutations consisting of base substitution mutation and frameshift mutation.

40. A method of claim 36 wherein the known mutation is due to the introduction of foreign DNA into the endogenous DNA of the mammalian cells at or near the specific site.

41. A method of claim 37 wherein the known mutation is due to the introduction of foreign DNA into the endogenous DNA of the mammalian cells at or near the specific site.

42. A method of claim 36 including the further step of introducing a selectable marker having a DNA sequence encoding a known selectable characteristic into the mammalian cells for conferring to the mammalian cells an additional selectable characteristic when cultured in the cell culture medium following mutagenic DNA reversion at or near the specific site.

43. A method of claim 42 wherein the mutated gene and selectable marker are introduced simultaneously into the mammalian cells by a method selected from a group of methods consisting of contransfection, transfection with the gene ligated to the selectable marker and microinjection.

44. A method of claim 36 including the further step of inserting a retrovirus proviral DNA or other transposable DNA at or near the selected site in the gene to generate the mutated gene, the mammalian cells being hemizygous or heterozygous at or near the specific site.

45. A method of claim 44 wherein the specific site is in or near the gene encoding adenine phosphoribosyltransferase (APRT) when in an unmutated form.

46. A method of claim 44 wherein the retrovirus proviral DNA is derived from murine leukemia virus.

47. A method of claim 36 wherei the medium is a cell culture medium containing adenine, alanosine, azaserine or any combination thereof.

48. A method of claim 36 wherein the mutated gene is a constructed mutated cloned gene encoding adenine phosphoribosyltransferase (APRT) when in an unmutated form.

49. A method of claim 48 wherein the mammalian cells are nonreverting mammalian cells that cannot revert to adenine phosphoribosyltransferase (APRT) producing cells absent undergoing specific DNA mutagenic reversion at the specific site in the gene.

50. An assay ensemble for determining whether an agent induces mutation in DNA in mammalian cells and characterizing the type of mutation induced thereby comprising an effective number of mammalian cells containing a gene which has been introduced into said mammalian cells, the gene having a known mutation introduced at or near a specific site, the gene having a DNA sequence encoding a known selectable characteristic when in an unmutated form and the mammalian cells being nonselectable for said characteristic when cultured in a cell culture selection medium absent undergoing mutagenic DNA reversion at or near the specific site, and an effective amount of the cell culture medium which selects for the mammalian cells which have undergone specific mutagenic DNA reversion at or near the specific site in the gene when exposed to an agent that has induced the mutation and characterizing the type of mutation induced by the agent.

51. An assay ensemble of claim 50 wherein the mutated gene encodes adenine phosphoribosyltransferase (APRT).

52. An assay ensemble of claim 51 wherein the mammalian cells are nonreverting mammalian cells that cannot revert to APRT producing cells absent undergoing mutagenic DNA reversion at or near the specific site.

53. An assay of claim 50 wherein the medium is cell culture medium containing adenine, alanosine, azaserine or any combination thereof.

54. An assay ensemble of claim 50 wherein the mammalian cells further include a selectable marker having a DN sequence encoding a known selectable characteristic for conferring to the mammalian cells an additional selectable characteristic when cultured in cell culture medium following mutagenic DNA reversion at or near the specific site.

55. An assay ensemble of claim 54 wherein the selectable marker is a plasmid containing a neomycin-resistance gene conferring G418 drug resistance to the mammalian cells as the additional selectable characteristic.

56. An assay ensemble of claim 50 wherein the mutated gene is a recombinant vector adapted for transforming the mammalian cells, the recombinant vector comprising a plasmid or phage into which a DNA segment encoding adenine phosphoribosyltransferase (APRT) has been inserted.

57. An assay ensemble of claim 56 wherein the plasmid or phage is a bacterial plasmid or phage and the DNA segment encodes APRT when in an unmutated form.

58. A kit for determining whether an agent induces base substitution, frameshift or DNA transposition mutation in DNA in mammalian cells comprising
(a) an effective number of at least one of the following types of mammalian cells selected from a group of mammalian cells consisting of
(i) mammalian cells containing an introduced mutated cloned gene having a base substitution at a specific site, the mutated cloned gene having a DNA sequence encoding a known selectable characteristic when the gene is in an unmutated form, the transfected mammalian cells being nonrevertable for the characteristic when in an untransfected form and nonselectable for said characteristic when cultured in a cell culture selection medium absent undergoing base substitution mutagenic reversion at the specific site,
(ii) mammalian cells containing an introduced mutated cloned gene having a frameshift mutation at a specific site, the mutated cloned selectable gene having a DNA sequence encoding a known selectable characteristic when the gene is in an unmutated form, the transfected mammalian cells being nonrevertable for the characteristic when in an untransfected form and nonselectable for said characteristic when cultured in a cell culture selection medium absent undergoing frameshift mutagenic reversion at the specific site, and
(iii) hemizygous or heterozygous mammalian cells containing a retrovirus proviral DNA or other transposable DNA at or near a specific site in a DNA segment of the hemizygous or heterozygous mammalian cells, the DNA segment having a DNA sequence encoding a known selectable characteristic when in an unmutated form and the retrovirus proviral DNA or other transposable DNA render the hemizygous or heterozygous mammalian cells nonselectable for said characteristic when cultured in a cell culture selection medium absent undergoing DNA mutagenic reversion at or near the specific site, and
(b) an effective amount of cell culture medium which selects for those mammalian cells that are selectable for said characteristic when cultured in said cell culture medium as a result of DNA mutagenic reversion at or near the specific site when exposed to an agent for identifying the agent as a mutagen which induces base substitution, frameshift or DNA transposition mutation in DNA in mammalian cells.

59. A kit of claim 58 wherein the introduced mutated cloned gene encodes adenine phosphoribosyltransferase (APRT) when in an unmutated form.

60. A kit of claim 59 wherein the mammalian cells are selected from a group of mammalian cells consisting of human mammalian cells that are nonrevertable for producing APRT when in an untransfected form and mouse mammalian cells that are nonrevertable for producing APRT when in an untransfected form.

61. A kit of claim 60 wherein the human cells are human recessive phenotype adenine phosphoribosyltransferase (APRT−) line HTD-114 cells.

62. A kit of claim 60 wherein the mouse cells are mouse recessive phenotype adenine phosphoribosyltransferase (APRT−) LS-24b or CAK cells.

63. A kit of claim 58 wherein the specific site is a Pst 1 restriction site at an intron/exon junction in a mouse gene encoding adenine phosphoribosyltransferase (APRT) when in an unmutated form.

64. A kit of claim 58 wherein the mammalian cells further comprise a selectable marker having a DNA sequence encoding a known selectable characteristic for conferring to the mammalian cells an additional selectable characteristic when cultured in a cell culture medium following DNA mutagenic reversion at or near the specific site.

65. A kit of claim 64 wherein the selectable marker is a plasmid containing a neomycin-resistance gene for conferring G418 drug resistance to the mammalian cells as the additional selectable characteristic.

66. A kit of claim 58 wherein the cell culture medium contains adenine, alanosine, azaserine or any combination thereof.

67. A kit of claim 58 wherein the frameshift reversion induced by the agent is same or second site frameshift reversion.

68. A kit of claim 58 wherein the retrovirus proviral DNA is derived from murine leukemia virus.

69. A kit of claim 58 wherein the introduced mutated cloned gene is a recombinant plasmid adapted for transforming the mammalian cells, the recombinant plasmid comprising a plasmid into which a DNA segment encoding adenine phosphoribosyltranferase (APRT) has been inserted.

70. A kit of claim 69 wherein the recombinant plasmid is pSAM-1 wherein the plasmid is bacterial plasmid pBR328 and the DNA segment encodes mouse APRT.

71. A kit of claim 58 wherein the introduced mutated selectable clone gene is a recombinant vector adapted for transforming the mammalian cells, the recombinant vector comprising a phage into which a DNA segment encoding human adenine phosphoribosyltransferase (APRT) has been inserted.

* * * * *

UNITED STATES PATENT AND TRADEMARK OFFICE
CERTIFICATE OF CORRECTION

PATENT NO. : 4,792,520  
DATED : December 20, 1988  
INVENTOR(S) : Peter J. Stambrook et al.

It is certified that error appears in the above-identified patent and that said Letters Patent is hereby corrected as shown below:

Column 5, lines 30-31, "wo-wuld" should be --would--.

Column 7, line 38, "Pst" should be --<u>Pst</u>--.

Column 7, line 58, "an" should be --and--.

Column 7, line 62, "NUcleic" should be --Nucleic--.

Column 8, line 18, "CTGCATGCT*" should be --CTGCAT/GCT--.

Column 8, lines 16-28, "CTGCAA/GCT" should be --CTGCA$\underline{A}$/GCT--; "CTGCGG/GCT" should be --CTGC$\underline{G}$G/GCT--; "CTGCAT/GCT" should be --CTGCA$\underline{T}$/GCT--; "CTGCAC/GCT" should be --CTGCA$\underline{C}$/GCT--; "CTGCAG/ACT" should be --CTGCAG/$\underline{A}$CT--; "CTGCAG/CCT" should be --CTGCAG/$\underline{C}$CT--; "CTGCAG/TCT" should be --CTGCAG/T$\underline{C}$T--; "5'TCCTGTCTGCAA/GCTGAG3'" should be --5'TCCTGT$\underline{C}$TGCAA/GCTGAG3'--; "5'TCCTGTCTGCGG/GCTGAG3'" should be --5'TCCTGTCTGC$\underline{G}$G/GCTGAG3'--; "5'TCCTGTCTGCAT/GCTGAG3'" should be --5'TCCTGTCTGCA$\underline{T}$/GCTGAG3'--; "5'TCCTGTCTGCAC/GCTGAG3'" should be --5'TCCTGTCTGCA$\underline{C}$/GCTGAG3'--; "5'TCCTGTCTGCAG/ACT3'" should be --5'TCCTGTCTGCA$\underline{G}$/ACT3'--; "5'TCCTGTCTGAAG/CCT3'" should be --5'TCCTGTCTGAAG/$\underline{C}$CT3'--; and "5'TCCTGTCTGAA/TCT3'" should be --5'TCCTGTCTGAA/T$\underline{C}$T3'--.

Column 8, line 43, "required" should be --repaired--.

Column 8, line 47, "plsmid" should be --plasmid--.

Column 9, line 26, "muse" should be --mouse--.

UNITED STATES PATENT AND TRADEMARK OFFICE
CERTIFICATE OF CORRECTION

PATENT NO. : 4,792,520

DATED : December 20, 1988

INVENTOR(S) : Peter J. Stambrook et al.

Page 2 of 5

It is certified that error appears in the above-identified patent and that said Letters Patent is hereby corrected as shown below:

Column 9, line 59, "Pst" should be --*Pst*--.

Column 9, line 67, "Pst" should be --*Pst*--.

Column 12, line 3, "cys" should be --*cys*--.

Column 12, line 4, "tyr" should be --*tyr*--.

Column 12, line 5, "tyr" should be --*tyr*--.

Column 12, line 7, "try" should be --*try*--.

Column 12, lines 26 and 28, "tyr" should be --*tyr*--.

Column 12, line 30, "cys" should be --*cys*--.

Column 12, lines 36-37, "dodecaptide" should be --dodecapeptide--.

Column 14, lines 3, 4, 6, 8 and 23, "SalI" should be --*Sal*I--.

Column 15, line 48, "abov" should be --above--.

Column 15, line 59, "Hin, Bam, Pvu" should be --*Hin*, *Bam*, *Pvu*--.

UNITED STATES PATENT AND TRADEMARK OFFICE
CERTIFICATE OF CORRECTION

PATENT NO. : 4,792,520  Page 3 of 5
DATED : December 20, 1988
INVENTOR(S) : Peter Stambrook et al.

It is certified that error appears in the above-identified patent and that said Letters Patent is hereby corrected as shown below:

Column 16, line 22, "Bam" should be --*Bam*--.

Column 16, line 66, "Bam" should be --*Bam*--.

Column 17, line 4, "65°Cl" should be --65°C--.

Column 17, line 10, "2" should be --20--.

Column 17, line 34, "Bam" should be --*Bam*--.

Column 17, line 36, "Eco" should be --*Eco*--.

Column 17, line 37, "Hind" should be --*Hind*--.

Column 17, line 37, "Sal" should be --*Sal*--.

Column 17, line 37, "Xba" should be --*Xba*--.

Column 17, line 37, "Bgl" should be --*Bgl*--.

Column 17, line 40, "Pst" should be --*Pst*--.

Column 17, line 40, "Pvu" should be --*Pvu*--.

Column 17, line 43, "Bam" should be --*Bam*--.

Column 17, line 44, "Bam" should be --*Bam*--.

Column 17, line 49, "Bam" should be --*Bam*--.

Column 17, line 53, "Eco" should be --*Eco*--.

UNITED STATES PATENT AND TRADEMARK OFFICE
CERTIFICATE OF CORRECTION

PATENT NO. : 4,792,520
DATED : December 20, 1988
INVENTOR(S) : Peter J. Stambrook et al.

It is certified that error appears in the above-identified patent and that said Letters Patent is hereby corrected as shown below:

Column 17, line 53, "Hind" should be --Hind--.

Column 17, line 54, "Bam" should be --Bam--.

Column 17, line 54, "Pst" should be --Pst--.

Column 17, line 54, "Pvu" should be --Pvu--.

Column 17, line 54, "Taq" should be --Taq--.

Column 17, line 56, "Tag" should be --Taq--.

Column 17, line 58, "Taq" should be --Taq--.

Column 17, line 58, "Bam" should be --Bam--.

Column 17, line 64, "Tag" should be --Taq--.

Column 17, line 67, "Bam" should be --Bam--.

Column 17, line 67, "Pst" should be --Pst--.

Column 17, line 67, "Tag" should be --Taq--.

Column 17, line 68, "Bgl" should be --Bgl--.

Column 17, line 68, "Pvu" should be --Pvu--.

Column 18, line 1, "Bam" should be --Bam--.

Column 18, line 3, "Tag" should be --Taq--.

UNITED STATES PATENT AND TRADEMARK OFFICE
CERTIFICATE OF CORRECTION

PATENT NO. : 4,792,520
DATED : December 20, 1988
INVENTOR(S) : Peter J. Stambrook et al.

It is certified that error appears in the above-identified patent and that said Letters Patent is hereby corrected as shown below:

Column 18, line 44, "clone" should be --cloned--.

Column 18, line 48, "APRA" should be --APRT--.

Column 18, line 50, "APRA" should be --APRT--.

Column 19, line 43, "cels" should be --cells--.

Column 20, line 61, "inserting" should be --insertion--.

Column 20, line 61, after "inserting" insert --rendering--.

Column 22, line 37, "wherei" should be --wherein--.

Column 23, line 13, "DN" should be -- DNA --.

Signed and Sealed this

Sixth Day of June, 1989

Attest:

DONALD J. QUIGG

Attesting Officer

Commissioner of Patents and Trademarks